United States Patent [19]
Oshita et al.

[11] Patent Number: 5,606,005
[45] Date of Patent: Feb. 25, 1997

[54] POLYURETHANE AND MOLDED ARTICLE COMPRISING THE SAME

[75] Inventors: Tatuya Oshita; Kimio Nakayama; Michihiro Ishiguro; Koji Hirai; Shigeaki Suzuki; Noriaki Yoshimura, all of Kurashiki, Japan

[73] Assignee: Kuraray Co., Ltd., Kurashiki, Japan

[21] Appl. No.: 558,779

[22] Filed: Nov. 16, 1995

[30] Foreign Application Priority Data

Nov. 16, 1994 [JP] Japan .................................. 6-282006
Dec. 28, 1994 [JP] Japan .................................. 6-327291
Mar. 3, 1995 [JP] Japan .................................. 7-044079

[51] Int. Cl.$^6$ ............................................. C08G 18/42
[52] U.S. Cl. ............................................. 528/83; 528/906
[58] Field of Search ........................................ 528/83, 906

[56] References Cited

U.S. PATENT DOCUMENTS 5,310,852  5/1994  Hirai et al. ............................ 528/83

FOREIGN PATENT DOCUMENTS 0271789  5/1987  European Pat. Off. .

OTHER PUBLICATIONS

Patent Abstracts of Japan, No. JP60026018, Aug. 2, 1985.
Patent Abstracts of Japan, No. JP920307927, Oct. 23, 1992.
Patent Abstracts of Japan, No. JP60199017, Aug. 10, 1985.
Patent Abstracts of Japan, No. JP4041715, Dec. 2, 1992.

*Primary Examiner*—Rachel Gorr
*Attorney, Agent, or Firm*—Oblon, Spivak, McClelland, Maier & Neustadt, P.C.

[57] ABSTRACT

A polyurethane made of polyester diol units, organic diisocyanate units and units from a chain extender, wherein the polyester diol units contain dicarboxylic acid units and diol units, wherein at least 30 mole % of the dicarboxylic acid units are units derived from 3,8-dimethyldecanedioic acid, 3,7-dimethyldecanedioic acid or a mixture thereof, and wherein the polyester diol units have a number-average molecular weight in a range from 500 to 6000 is provided along with the polyester diol for preparing the polyurethane, polyurethane fibers prepared from the polyurethane, a molded article prepared from the polyurethane and processes for producing the polyurethane, polyester diol, dimethyldecanedioic acids and dimethyldecanedials used to prepare the dimethyldecanedioic acids; where the polyurethane and fibers produced therefrom are superior in various properties such as hydrolytic resistance, heat resistance, resistance to hot water, cold resistance, fungal resistance and mechanical performances e.g., strength at break and elongation at break, as well as injection moldability and the fibers are dyeable under high-temperature and high-pressure conditions and are superior, after dyeing, in tensile strength and elongation, elastic recovery, fungal resistance, resistance to chlorine and color fastness.

5 Claims, No Drawings

POLYURETHANE AND MOLDED ARTICLE COMPRISING THE SAME

BACKGROUND OF THE INVENTION

1. Field of the Invention

The present invention relates to a polyurethane having superior hydrolytic resistance, heat resistance, resistance to hot water, cold resistance, fungal resistance, mechanical performances, as well as in injection moldability, and which is useful as a material for molding, fibers and molded article comprising the same, and starting materials for preparing the polyurethane.

2. Discussion of the Background

Polyurethanes have many advantageous characteristics such as high elasticity, excellent wear and abrasion resistance, and oil resistance, and have thus been used in a wide variety of end uses, such as a replacement for rubber and other plastics.

Various types of polyurethanes are known, such as polyether-based polyurethanes, polyester-based polyurethanes and polycarbonate-based polyurethanes. These polyurethanes are widely used in the production of fibers, sheets, films, adhesives, coating agents and the like. Among these conventional polyurethanes, the polyether-based ones are superior in resistance to hydrolysis, but inferior in resistance to light, resistance to heat aging and resistance to chlorine. The polyester-based polyurethanes are superior in mechanical characteristics and wear and abrasion resistance in comparison with the polyether-based ones, but are inferior in resistance to hydrolysis and fungal resistance. Use of the polyester-based polyurethanes is limited because the surface thereof becomes adhesive or cracks within a relatively short period of time. The polycarbonate-based polyurethanes possess the same advantages described above for the polyester-based polyurethanes, and further possess superior durability. However, they are inferior in cold resistance, and are extremely expensive.

In order to improve the hydrolytic resistance of the polyester-based polyurethanes, it has been considered effective to decrease the concentration of ester groups from the polyester diol used for producing the polyurethanes. The following polyurethanes have been proposed for this purpose: (1) a polyurethane using a polyester diol, as raw material, obtained by using hexamethylene glycol and 1,10decanediol (see Japanese Patent Application Laid-open No. 173117/1985); (2) a polyurethane using, as raw material, a polyester diol comprising 2,2,4- or 2,4,4-trimethylhexanediol and adipic acid (see Japanese Patent Application Laid-open No. 713/1972); (3) a polyurethane using, as raw material, a polyester diol obtained by using 2,5-hexanediol or 2,2-dimethyl-1,3propanediol (see U.S. Pat. No. 3,097, 192); and (4) a polyurethane using (2,2-dimethyl-1,3-propanedodecanedioate) glycol (see Japanese Patent Application Laid-open No. 97617/1988) .

In order to improve the hydrolytic resistance of polyester-based polyurethanes, a polyester diol which contains branched dicarboxylic acid units having one methyl side-chain has been used as a raw material to make polyurethane. For example, the following polyurethanes have been proposed: (5) a polyurethane prepared using a polyester diol and obtained by reacting a dicarboxylic acid containing 3-methylpentanedioic acid and a glycol (see Japanese Patent Application Laid-open No. 26018/1985); and (6) a polyurethane prepared using a polyester diol and containing 10 mole % or more of 2-methyloctanedioic acid of total dicarboxylic acid units (see Japanese Patent Application Laid-open No. 320302/1993).

However, with the polyurethanes described above in (1) through (4), the hydrolytic resistance is improved, but the cold resistance and low temperature characteristics such as flex resistance and flexibility decrease extremely upon standing at low-temperature because these polyurethanes have a strong tendency to crystallize. The polyurethane described in (1) obtained by using a diol having a long linear chain has the further disadvantage of low elastic recovery. The polyurethanes described in (2) through (4) using a diol having two or three methyl groups as side-chains have the further disadvantages of poor heat resistance, poor elastic recovery and poor cold resistance. Compared with conventional polyurethanes, the polyurethanes described in (5) and (6) are improved in hydrolytic resistance but are still insufficient in hydrolytic resistance and the cold resistance, heat resistance and injection moldability thereof are also considered to be at insufficient levels for practical purposes. Furthermore, compared with conventional polyurethane fibers, polyurethane fibers described in (5) and (6) are improved in heat resistance, resistance to hot water, elastic recovery, and cold resistance, but still not to a sufficient level for practical purposes. Thus, difficulties arise when these polyurethane fibers are used in combination with polyester fiber and the like, and are dyed stably and industrially with disperse dye under high-temperature and high-pressure conditions. Furthermore, the tensile strength and elongation, elastic recovery resistance to chlorine, color fastness and the like of these polyurethanes after dyeing are not sufficient for practical purposes.

As processes for synthesizing 3,8- or 3,7-dimethyldecanedioic acid, the following (7) through (9) are known: (7) a process for synthesizing 3,8-dimethyldecanedioic acid, from 2,7-octanedione comprising the five steps of Reformatsky reaction of ethyl bromoacetate, bromination of hydroxyl group, dehydrobromination, hydrogenation of double bond and hydrolysis of ester (see Ann., 580, 125–131 (1953)); (8) a process for synthesizing 3,8-dimethyldecanedioic acid, comprising seven steps starting from malonic condensation of diethyl methylmalonate and 1,4-dibromobutane, followed by hydrolysis and decarboxylation to obtain 2,7-dimethyloctanedioic acid as an intermediate and the subsequent conversion of this intermediate to acid chloride, which is then converted via diazoketone into the intended dicarboxylic acid (see Ann., 598, 1–24 (1956)); (9) a process to obtain 3,7-dimethyldecanedioic acid by hydrogenation of essential oil of *Geranium macrorhizum*, and subsequent ozonolysis and degradation with perchloric acid (see Chem.listy, 52, 1174–1179 (1958)).

Neither of the processes for synthesizing 3,8-dimethyldecanedioic acid described in (7) and (8) above is an industrially useful process, because many reaction steps are required, and expensive or hazardous to handle raw materials or reagents are required. The process for synthesizing 3,7-dimethyldecanedioic acid described in (9) above is also not an industrially useful process, because a natural essential oil is used as a raw material, and explosive ozone or perchloric acid is used as a reagent. Therefore, it has been strongly desired to develop a process for economically producing 3,8- or 3,7-dimethyldecanedioic acid with inexpensive raw materials and reagents through a short process.

SUMMARY OF THE INVENTION

Accordingly, one object of the present invention is to provide a polyurethane which is superior in various properties such as hydrolytic resistance, heat resistance, resistance to hot water, cold resistance, fungal resistance and mechanical performance, as well as in injection moldability.

A further object of the present invention is to provide a polyurethane useful as a material for various molded articles; and a molded article comprising the polyurethane.

A further object of the present invention is to provide a polyurethane fiber which has excellent heat resistance, resistance to hot water, resistance to hydrolysis and like properties, is dyeable under high- temperature and high-pressure conditions and, after dyeing, is superior in tensile strength and elongation, elastic recovery, fungal resistance, resistance to chlorine and color fastness.

A further object of the present invention is to provide a polyester diol which is useful as a raw material in the production of such polyurethanes.

A further object of the present invention is to provide a short process for economically producing 3,8- or 3,7-dimethyldecanedioic acid, which is useful as a raw material to produce such polyester diols, using inexpensive raw materials and reagents.

A further object of the present invention is to provide novel dimethyldecanedials which can economically give 3,8- or 3,7-dimethyldecanedioic acid and a process for producing the same.

These and other objects of the present invention have been satisfied by the discovery of a polyurethane comprising a polyester diol component, an organic diisocyanate component and a chain extender component, wherein the polyester diol comprises 30 mole % or more of dicarboxylic acid units selected from the group consisting of 3,8- and/or 3,7-dimethyldecanedioic acid units, and wherein the polyester diol has a number-average molecular weight of 500 to 6000;

and a molded article and polyurethane fiber, each comprising said polyurethane.

The present invention further provides a polyester diol, wherein 30 mole % or more of the dicarboxylic acid units constituting said polyester diol are 3,8- and/or 3,7-dimethyldecanedioic acid units, and wherein the polyester diol has a number-average molecular weight of 500 to 6000; and a process for producing dimethyldecanedioic acids represented by the general formula (II) comprising oxidizing dimethyldecanedials represented by the general formula (I);

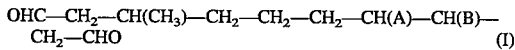

wherein either of A and B represents a methyl group and the other represents a hydrogen atom,

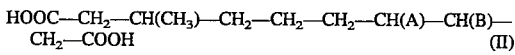

wherein either of A and B represents a methyl group and the other represents a hydrogen atom, and the dimethyldecanedials represented by the general formula (I).

The present invention yet further provides a process for producing the dimethyldecanedial represented by the general formula (I) comprising hydroformylation of a diolefin represented by the general formula (III).

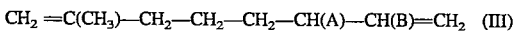

wherein either of A and B represents a methyl group and the other represents a hydrogen atom.

DETAILED DESCRIPTION OF THE PREFERRED EMBODIMENTS

The polyurethane of the present invention is markedly superior in various properties e.g., hydrolytic resistance, heat resistance, resistance to hot water, cold resistance, fungal resistance, and mechanical performance such as tensile strength, elongation at break, and is excellent in injection moldability as well.

The polyurethane fiber of the present invention is superior in heat resistance, resistance to hot water, cold resistance and hydrolytic resistance, and is dyeable under high-temperature and high-pressure conditions. This fiber is also excellent in tensile strength and elongation after dyeing, elastic recovery, fungal resistance and resistance to chlorine.

The dimethyldecanedials of the present invention are useful as a raw material for producing the dimethyldecanedioic acids represented by the general formula (II). The polyester diol containing the dimethyldecanedioic acid as the dicarboxylic acid component shows excellent hydrolytic resistance and is useful as a raw material for producing the high-performance polyurethanes.

The dimethyldecanedials of the present invention represented by the general formula (I) can be produced by hydroformylation of a diolefin represented by the general formula (III). As an example, 3,8-dimethyldecanedial (represented by the general formula (I) when A=H and B=Me) can be produced by hydroformylation of 2,7-dimethyl-1,7-octadiene (represented by the general formula (III) when A=H and B=Me) using a mixed gas of carbon monoxide and hydrogen in the presence of a catalyst, and 3,7-dimethyldecanedial (represented by the general formula (I) when A=Me and B=H) can be produced, in the same way as the above, from 2,6-dimethyl-1,7-octadiene (represented by the general formula (III) when A=Me and B=H).

2,7-dimethyl-1,7-octadiene and 2,6-dimethyl-1,7-octadiene can be produced from isoprene, a formic acid salt and water by action of a palladium catalyst (see Japanese Patent Publication No. 41576/1987 and Japanese Patent Application Laid-open No. 157521/1980, respectively).

As the catalyst for the reaction to produce the dimethyldecanedials of the present invention represented by the general formula (I), any olefin hydroformylation catalyst is usable, but those containing an element belonging to Group VIII of the Periodic Table alone or in combination with a phosphorus compound or nitrogen compound are preferred, with catalysts comprising a rhodium compound and phosphorus compound being particularly preferred.

Any rhodium compound having catalytic activity for hydroformylation or capable of being activated in situ within the hydroformylation reactor can be preferably used. Suitable rhodium compounds include inorganic salts such as rhodium oxide, rhodium chloride and rhodium bromide; carboxylic acid salts such as rhodium acetate and rhodium propionate; chelate compounds such as rhodium acetylacetonate; carbonyl compounds such as $Rh_4(CO)_{12}$, $[Rh(CO)_2Cl]_2$ and $Rh(CO)_2(CH_3COCHCOCH_3)$; and metals such as Rh/C, Rh/silica, Rh/alumina and Rh black. The amounts used of these compounds, which vary depending on the kind and amount of the phosphorus compound used, or on the reaction conditions, are in a range of from 0.005 to 5 mg-atom/liter, preferably in a range of from 0.1 to 0.5 mg-atom/liter in terms of the concentration of rhodium atoms in the reaction mixture.

As the phosphorus compound used in combination with the above rhodium compound, any phosphorus compound capable of increasing the catalytic activity and/or improving catalyst life in comparison with use of the rhodium compound alone is usable. Preferred phosphorus compounds include phosphines such as tributylphosphine, tricyclohexylphosphine, triphenylphosphine, tri(o-tolyl)phosphine, sodium m-diphenylphosphinobenzenesulfonate, diphenylphosphinoethane, diphenylphosphinopropane, and diphenylphosphinobutane; phosphites such as triethyl phosphite, trimethylolpropane phosphite, triphenyl phosphite, tri(o-tolyl) phosphite, tri(2-t-butylphenyl) phosphite, tris(2, 6-di-t-butylphenyl) phosphite. The amounts used of these organic phosphorus compounds are in a range of from 1 to 1000 mole per 1 g-atom of rhodium, preferably in a range of from 10 to 500 mole per 1 g-atom of rhodium and particularly preferably in a range of from 50 to 300 mole per 1 g-atom of rhodium.

The reaction to produce the dimethyldecanedials of the present invention represented by the general formula (I) is preferably conducted at a temperature ranging from 60° to 150 ° C., most preferably from 90° to 130° C. When the reaction temperature is lower than 60° C., the rate of the reaction becomes low; and when it exceeds 150° C., maintenance of the catalytic stability becomes difficult.

The reaction pressure, which is dependent on the reaction temperature, is preferably in a range of from 10 to 150 atm, most preferably in a range of from 60 to 120 atm. When the reaction pressure is lower than 10 atm, the reaction rate and the selectivity are lowered. Although there is no specific upper limit on the reaction pressure, pressures below 150 atm are industrially preferable to conduct the reaction in view of reaction apparatus and operability.

The ratio between the carbon monoxide and hydrogen used in the reaction is preferably in a range of carbon monoxide/hydrogen=1/3 to 3/1 as the molar ratio of the gases fed to the reaction vessel. One or more additional gases inert to the hydroformylation reaction may be used, if desired.

A solvent is not always necessary for the reaction but may be used as long as the solvent does not adversely affect the hydroformylation reaction. Examples of suitable solvents include hydrocarbons such as hexane, cyclohexane, benzene, toluene, and xylene; ethers such as dibutyl ether, tetrahydrofuran, dioxane, ethylene glycol dimethyl ether and polyethylene glycol dimethyl ether; esters such as methyl acetate, ethyl acetate, and butyl acetate; alcohols such as ethanol, isopropyl alcohol, n-butanol, t-butanol, ethylene glycol, diethylene glycol and polyethylene glycol; amides such as N,N-dimethylformamide and N-methylpyrrolidone; and sulfur-containing compounds such as dimethyl sulfoxide and sulfolane. The amount of the solvent used is arbitrary but, in view of capacity efficiency, amounts less than 50 parts by weight based on that of the raw material olefin represented by the general formula (III) are preferred.

The reaction can be conducted either batchwise or continuously. When conducted bachwise, either of the following procedures can be used; (i) a procedure comprising charging catalyst components, the diolefin represented by the general formula (III) and a solvent, if desired, followed by pressurizing with a mixed gas of carbon monoxide and hydrogen, and then reacting at a prescribed temperature; or (ii) a procedure comprising feeding catalytic components and a solvent to the reaction vessel followed by pressurizing with carbon monoxide and hydrogen and raising the temperature, then feeding the diolefin represented by the general formula (III) or, if necessary, a mixture thereof with a solvent.

The reaction can be conducted to a conversion of either 100 % or less. After the reaction, carbon monoxide and hydrogen are purged, the solvent is recovered by distillation (if desired) and then the dimethyldecanedials represented by the general formula (I) are obtained through purification means such as distillation, film evaporation, steam distillation or extraction. The catalyst components separated through the purification process are reusable.

From the dimethyldecanedials thus obtained, represented by the general formula (I), the dimethyldecanedioic acids represented by the general formula (II) can be produced by oxidation. This can be conducted by any usual method known for conversion of aldehyde to carboxylic acid, including, but not limited to, oxidation with oxygen in the presence of a metal salt as a catalyst. The dimethyldecanedials represented by the general formula (I) can be subjected to the above oxidation either after or without purification by means mentioned above.

As a catalyst for the production of a dimethyldecanedioic acid of formula (II) from a dimethyldecanedial of formula (I) there can be used transition metals such as copper, cobalt, manganese and iron; their halides such as chlorides, bromides and iodides; carboxylic acid salts such as acetic acid salts, propionic acid salts and 2-ethylhexanoic acid. salts; and diketone complexes such as acetylacetonate. These metals or metal salts can be used singly or in a combination of two or more, and the metal salts may be in either hydrous or anhydrous form. The amount used of these catalysts, which varies depending on the reaction conditions, is in a range of from 0.1 to 1000 ppm, preferably in a range of from 1 to 100 ppm in terms of the concentration of the metal atom in the reaction mixture.

The reaction need not always use a solvent, but a solvent can be used so long as it is inert to the oxidation reaction. Usable solvents include carboxylic acids such as acetic acid and propionic acid; and water. They can be used singly or in a combination of two or more. The amount of solvent used is arbitrary but, in view of capacity efficiency, amounts not more than 50 parts by weight based on the amount of dimethyldecanedial of formula (I) as raw material are suitable.

It is preferable to conduct the oxidation of the dimethyldecanedials of formula (I) at a temperature ranging from 10° to 100° C., preferably from 30° to 80° C. which also depends on the melting point of the reaction mixture. When the reaction temperature is lower than 30° C., the reaction rate becomes low; and when it exceeds 80° C., control of the reaction tends to become difficult.

The oxidation reaction can be conducted in oxygen or a mixture thereof with an inert gas, such as air. It is industrially preferred to use air. There is no particular upper limit on the reaction pressure, but it is preferable to conduct the reaction at a pressure lower than 50 atm, most preferably lower than 10 atm in view of the reaction apparatus and safety.

The reaction can be conducted either batchwise or continuously. When conducted batchwise, the following procedures can be used: a procedure comprising charging the catalyst, the dimethyldecanedials of formula (I) and a solvent, if desired, and conducting the reaction at a prescribed temperature and pressure in the presence of oxygen or a mixture of oxygen and inert gas, such as air; or a procedure comprising, feeding the dimethyldecanedials of formula (I) singly or, if necessary, as a mixture thereof with a solvent to the reaction used, while maintaining the reaction vessel charged with the catalyst and a solvent, at a prescribed temperature and pressure in the presence of oxygen or a mixture of oxygen and an inert gas, such as air. In either of the procedures, oxygen or a mixture of oxygen and an inert gas may be used either staticwise or flowwise.

The oxidation reaction can be performed to a conversion of either 100% or less. After the reaction, the dimethyldecanedioic acids of formula (II) are obtained through a procedure comprising purging the gas in the system, followed by recovering the solvent by distillation, if necessary, and then purification by means of crystallization, distillation, film evaporation, steam distillation, extraction or the like.

The polyester diol of the present invention substantially comprises diol units and dicarboxylic acid units. The content of 3,8-dimethyldecanedioic acid units and/or 3,7-dimethyldecanediaic acid units in the dicarboxylic acid units constituting the polyester diol of the present invention is necessarily at least 30 mole %, preferably at least 50 mole % and more preferably at least 80 mole %. When the content of 3,8-dimethyldecanedioic acid units and/or 3,7-dimethyldecanedioic acid units is less than 30 mole % of the dicarboxylic acid units constituting the polyester diol, the polyurethane obtained is inferior in hydrolytic resistance, fungal resistance, resistance to hot water and cold resistance. The ratio of 3,8-dimethyldecanedioic acid units and 3,7-dimethyldecanedioic acid units (molar ratio) is not specifically limited, but in view of hydrolytic resistance, fungal resistance and resistance to hot water of the obtained polyurethane, the ratio is preferably in a range of (3,8):(3,7) of from 50:50 to 100:0, more preferably in a range of from 70:30 to 100:0.

As the dicarboxylic acid units constituting the polyester diol, there may be contained units other than 3,8-dimethyldecanedioic acid units or 3,7-dimethyldecanedioic acid units and derived from acids such as saturated aliphatic dicarboxylic acids such as glutaric acid, adipic acid, pimelic acid, suberic acid, azelaic acid and sebatic acid; saturated alicyclic dicarboxylic acids such as cyclohexane dicarboxylic acid; aromatic dicarboxylic acids such as phthalic acid, terephthalic acid and isophthalic acid; unsaturated aliphatic dicarboxylic acids such as maleic acid, fumaric acid and itaconic acid; halogen-containing dicarboxylic acids such as tetrabromophthalic acid; or units derived from ester forming derivatives of the foregoing, such as esters and anhydrides thereof. These components may be contained singly or in a combination of two or more, provided that the content thereof is less than 70 mole % based on that of the total carboxylic acid units constituting the polyester diol. Furthermore, if necessary, units derived from a polybasic acid having three or more functionalities, such as trimellitic acid and pyromellitic acid may be contained in a small amount.

Examples of suitable diol units constituting the polyester diol include aliphatic diols such as ethylene glycol, propylene glycol, 1,3-propanediol, 1,4-butanediol, 1,5-pentanediol, neopentyl glycol, 1,6-hexanediol, 1,7-heptanediol, 1,8-octanediol, 1,9-nonanediol, 1,10-decanediol, 3-methyl-1,5-pentanediol and 2-methyl-1,8-octanediol; and alicyclic diols such as cyclohexanedimethanol and cyclohexanediol. These units may be contained singly or in a combination of two or more. It is preferable that units from 1,4-butanediol be contained in an amount of at least 30 mole more preferably at least 50 mole % and most preferably at least 80 mole % of total diol units constituting the polyester diol, since the solidification rate of the resulting polyurethane when molded becomes fast, and the heat resistance and resistance to hot water are excellent. If necessary, units derived from a polyalcohol such as trimethylolethane, trimethylolpropane, glycerine, 1,2,6-hexatriol and pentaerythritol may also be contained in a small amount.

The number average molecular weight of the polyester diol is in a range of from 500 to 6000, preferably in a range of from 1000 to 4000 and more preferably in a range of from 1000 to 3500. When the number average molecular weight is less than 500, the heat resistance, resistance to hot water and moldability of the polyurethane is lowered; while when the number average molecular weight exceeds 6000, the tensile elongation, elastic recovery, injection moldability and other properties of the polyurethane become inferior. The number average molecular weight herein is calculated based on the hydroxyl group value determined in accordance with JIS K 1577.

The polyester diol is produced by polycondensation of the carboxylic acid component and diol component described above through conventional ester exchange reaction, direct esterification or the like. The polycondensation can be conducted in the presence of a titanium-based or tin-based polycondensation catalyst. When a titanium-based polycondensation catalyst is used, it is preferable to deactivate the catalyst contained in the polyester diol after the reaction.

Any of the titanium-based polycondensation catalysts conventionally used for production of polyester diols can be used in the present invention with no specific limitation. Examples of preferred titanium-based polycondensation catalysts include titanium acid, tetraalkoxy titanium compounds, titanium acylate compounds, and titanium chelate compounds. More specifically, the titanium compounds include tetraalkoxy compounds such as tetraisopropyl titanate, tetra-n-butyl titanate, tetra-2-ethylhexyl titanate and tetrastearyl titanate; titanium acylate compounds such as polyhydroxy titanium stearate and polyisopropoxy titanium stearate; and titanium chelate compounds such as titanium acetylacetonate, triethanolamine titanate, titanium ammonium lactate, titanium ethyllactate and titanium octylene glycolate.

The amount of the titanium-based polycondensation catalyst is not specifically limited and can be suitably controlled according to intended polyester diol and the quality of the polyurethane produced therefrom. This amount is preferably in a range of from about 0.1 to about 50 ppm Ti metal based on total weight of reacting components to form the polyester diol, more preferably in a range of from about 1 to about 30 ppm Ti metal on the same basis.

Deactivation of the titanium-based polycondensation catalyst contained in the polyester diol can be achieved through a process which comprises contacting the polyester diol, after completion of esterification, with hot water with heating or through a process which comprises treating the polyester diol with a phosphorus compound, such as phosphoric acid, a phosphoric acid ester, phosphorous acid or a phosphorous acid ester. In the case of contacting the catalyst with hot water, it is recommended to add 1 weight % or more of water to the polyester diol obtained through the esterification reaction, and then heating the mixture at a temperature ranging from 70° to 150° C., preferably ranging from 90° to 130° C., for 1 to 3 hours. The deactivation treatment of the titanium-based polycondensation catalyst may be conducted under either an atmospheric pressure or a pressurized condition. It is preferable to reduce the pressure of the system after deactivation of the catalyst, in order to remove the water used for deactivation.

When the polyurethane of the present invention is produced, if necessary a polymer diol other than the polyester diol, such as polycarbonate diol may be used in a small amount.

There is no specific limitation to the type of the organic diisocyanate used for producing the polyurethane of the present invention, and any organic diisocyanate conventionally used for producing polyurethanes is usable. The organic diisocyanate used preferably has a molecular weight of not higher than 500. Examples of suitable organic diisocyanates include aromatic diisocyanates such as 4,4'-diphenylmethane diisocyanate, p-phenylene diisocyanate, tolylene diisocyanate, 1,5-naphthalene diisocyanate, 3,3'-dichloro-4,4'-diphenylmethane diisocyanate and xylylene diisocyanate, and aliphatic and alicyclic diisocyanates such as hexamethylene diisocyanate, isophorone diisocyanate, 4,4'-dicyclohexylmethane diisocyanate and hydrogenated xylylene diisocyanate. These diisocyanates may be used singly or in a combination of two or more. 4,4'-diphenylmethane diisocyanate or p-phenylene diisocyanate are particularly preferred. If desired, polyisocyanates having 3 or more functionalities, such as triphenylmethane triisocyanate are usable in a small amount.

As the chain extender used for producing the polyurethane of the present invention, any chain extender conventionally used for producing polyurethanes is usable, with no specific limitation, but use of a low molecular-weight-compound having a molecular weight of not more than 300 and having at least two hydrogen atoms reactive with an isocyanate group is preferable. Examples of preferred chain extenders include diols such as ethylene glycol, 1,4-butanediol, 1,6-hexanediol, 1,4-bis($\beta$-hydroxyethoxy)benzene, 1,4-cyclohexanediol, bis($\beta$-hydroxyethyl)terephthalate and xylylene glycol; diamines such as hydrazine, ethylenediamine, propylenediamine, xylylenediamine, isophorone diamine, piperazine, a piperazine derivative, phenylenediamine, tolylenediamine, adipic dihydrazide and isophthalic dihydrazide; and amino alcohols such as aminoethyl alcohol and aminopropyl alcohol. These compounds may be used singly or in a combination of 2 or more. Among these, 1,4-butanediol, 1,4-bis($\beta$-hydroxyethoxy)benzene, ethylenediamine and propylenediamine are preferred.

The amount used of the chain extender is not specifically limited and is suitably selected depending on the desired hardness and other physical properties to be given to the polyurethane, but usually, it is preferable to use the chain extender in a ratio ranging from 0.1 to 10 mole per mole of the polyester diol, especially preferable in a ratio ranging from 0.3 to 7 mole per mole of the polyester diol.

In the production of the polyurethane, it is recommended to use an organic diisocyanate in such an amount as to permit the ratio between the equivalents of isocyanate groups present in the organic diisocyanate and the total amount of active hydrogen atoms (present in the polyester diol, chain extender and other polymer diol used if necessary) to fall preferably within a range of from 0.90 to 1.20, more preferably within a range from 0.95 to 1.15. By use of the organic diisocyanate in such a ratio, the resulting polyurethane becomes especially superior in heat resistance and elastic recovery.

When the polyurethane is produced by using the above polyester diol, organic diisocyanate, chain extender and if necessary other components, a tin-based urethanization catalyst having catalytic activity for urethanization can be used. When a tin-based urethanization catalyst is used, the molecular weight of the resulting polyurethane increases rapidly, and the polyurethane becomes excellent in various physical properties, because the molecular weight of the polyurethane is maintained in a sufficiently high level even after molding. Examples of suitable tin-based urethanization catalysts include dialkyltin dialkylates such as dibutyltin diacetate and dibutyltin dilaurate; and dialkyltin bismercaptocarboxylic acid ester salts such as dibutyltin bis(3-mercaptopropionic acid ethoxybutyl ester)salt. The amount of these tin-based urethanization catalysts used is preferably in a range of from 0.5 to 15 ppm in terms of tin atom, based on the obtained polyurethane (that is, total weight of all reactive raw compounds such as the polyester diol, organic diisocyanate and chain extender used for producing the polyurethane).

If desired, either during or after polymerization of the polyurethane, 1 or more of additives such as coloring agent, lubricant, crystallization nucleus agent, flame retardant, ultra-violet absorber, antioxidant, weatherability improver, hydrolysis preventing agent, tackifier and mildew-proofing agent can be added.

There are no specific restrictions with respect to the process for producing the polyurethane and conventional urethanization processes can be used. Such conventional processes include using the above polyester diol, organic diisocyanate, chain extender and, as necessary, other components with either the prepolymer process or one-shot process.

Examples of the process for producing the polyurethane include (1) mixing a polyester diol and low-molecular-weight compound (chain extender) having active hydrogen atoms, heating the mixture, adding an organic diisocyanate to the mixture, stirring the resulting mixture for a short period of time and then heating the mixture to obtain the polyurethane; (2) mixing the polyester diol, chain extender and organic diisocyanate, and kneading the mixture at a high temperature (e.g., from 180° to 260° C.) to obtain the polyurethane; (3) continuously feeding the polyester diol, chain extender and organic diisocyanate to an extruder, such as a multi-screw extruder, and subjecting the resulting mixture to a continuous melt-polymerization at a high temperature (e.g., from 180° to 260° C.) to obtain the polyurethane; and (4) reacting the polyester diol, chain extender and organic diisocyanate to form the polyurethane, in an organic solvent (e.g., dimethylformamide, dimethylacetamide, dimethyl sulfoxide, tetrahydrofuran, toluene, methyl ethyl ketone, ethyl acetate, isopropanol, ethyl cellosolve and N-methylpyrolidone). Further, this list is not all inclusive and any other process for producing a polyurethane from the specified components can be used.

Among the above processes for producing the polyurethane, the processes of (1) through (3) which comprise melt-polymerizing the polyester diol, chain extender and organic diisocyanate with substantially no solvent are preferable, with the continuous melt polymerization of (3) using a multi-screw extruder being most preferred.

The inherent viscosity of the polyurethane of the present invention, as determined at 30° C. by measurement of a 0.5 g/dl polyurethane solution in N,N-dimethylformamide solution containing 0.05 mole/L of n-butylamine is preferably in a range of from 0.3 to 2.0 dl/g, more preferably in a range of from 0.5 to 2.0 dl/g, still more preferably in a range of from 0.8 to 2.0 dl/g, and most preferably in a range of from 1.0 to 2.0 dl/g. The polyurethane having an inherent viscosity of 0.3 to 2.0 dl/g is superior in mechanical performance, hydrolytic resistance, heat resistance, elastic recovery, cold resistance and other physical and chemical properties.

The polyurethane of the present invention, is useful as a material for a wide variety of end uses such as sheets, films, squeeze, chains, belts, screens, cleaning blade for copier, various rolls, gears, casters, solid tires, hoses, tubes, packings, vibration insulators, vibration dampers, shoe soles, sports shoes, machine parts, automobile parts, sporting goods, fibers, artificial leathers, fiber treatments, adhesives, coating agents, binders and paints.

As a process for producing the polyurethane fiber of the present invention by using the above desired polyurethane, it is possible to use any conventional process for producing polyurethane fibers, including but not limited to dry spinning, wet spinning or melt spinning. Preferable spinning processes include (A) a process which comprises producing a polyurethane by melt-polymerizing polyester diol, chain extender and organic diisocyanate containing substantially no solvent through a multi-screw extruder or the like and directly extruding the resultant polyurethane into filaments through a spinning nozzle directly connected to the multi-screw; and (B) a process which comprises producing a polyurethane through melt polymerization, pelletizing the polyurethane and then melt-spinning the pellet into filaments. In view of spinning stability, etc., the process of (A) is especially preferred. When the polyurethane fiber is produced through melt spinning, it is preferable to set the spinning temperature not higher than 250° C., more preferably between 200° and 235° C.

The polyurethane fiber of the present invention is usable as either neat fiber as it is or as either the core or sheath in a core-sheath yarn construction, with the other portion of the yarn being a conventional fiber such as polyamide, wool, cotton or polyester.

In general, in order to dye polyester and similar fibers, it is necessary to use a disperse dye, a high temperature of 110° C. or more and a high pressure. Therefore, conventional polyurethane fibers having only poor heat resistance and resistance to hot water are difficult to dye under such high temperature and high pressure conditions together with polyester fibers used in combination therewith. On the other hand, the polyurethane fiber of the present invention is dyeable under high temperature and high-pressure conditions due to superior heat resistance and resistance to hot water. Thus, the present polyurethane fibers can be dyed even after being processed by mixing with other fibers such as polyester fibers, by the use of disperse dye workable only at a high temperature such as 110° to 130° C. and a high pressure. Furthermore, the polyurethane fiber of the present invention maintains superior tensile strength and elongation, elastic recovery and like properties even after dyeing. Through dyeing with a conventional disperse dye under high-temperature and high-pressure, the polyurethane fiber of the present invention becomes colored to the same degree as that of other fibers, such as polyester fibers with which it is mixed and is improved in visual indistinguishability, color reproducibility and color fastness. Examples of suitable disperse dyes used in this case are quinone-type and azo-type disperse dyes. After being dyed with a disperse dye, it is preferable to conduct reduction cleaning to accelerate fixing of the dye.

Examples of end uses of the polyurethane fiber of the present invention include clothing such as swimsuits, skiwear, cycling wear, leotards, lingerie, foundation garments, underwear, panty hose, stockings; clothing accessories such as supporters, caps, gloves, power nets and bandages; and non-clothing items such as gut for tennis rackets, ground thread for integrally molded car seat, metal covered yarn for robot arms, bands for packaging and conveyor belts.

Having generally described this invention, a further understanding can be obtained by reference to certain specific examples which are provided herein for purposes of illustration only and are not intended to be limiting unless otherwise specified.

EXAMPLES

In the Examples and Comparative Examples that follow, the following methods were used to determine the number average molecular weight and hydrolytic resistance of the polyester diol; inherent viscosity, hydrolytic resistance, heat resistance, cold resistance, mechanical performance and injection moldability of the polyurethane; and the inherent viscosity, tensile strength and elongation, elastic recovery, hydrolytic resistance, resistance to hot water, cold resistance, color fastness, tensile strength and elongation after dyeing, elastic recovery and resistance to chlorine of the polyurethane fiber.

Number average molecular weight of polyester diol

JIS K 1577 was applied to determine the hydroxyl group value, from which the molecular weight was calculated.

Hydrolytic Resistance of polyester diol

A polyester diol sample was immersed in hot water of 100°° C. for 10 days, and then the acid value was determined to evaluate resistance to hydrolysis.

Inherent viscosity of polyurethane or the fiber thereof

A polyurethane or its fiber sample was dissolved in a concentration of 0.5 g/dl in N,N-dimethylformamide solution containing n-butylamine in a concentration of 0.05 mole/L, and then the resultant solution was subjected to observation for a time of fall with an Ubbellohde viscometer, from which the viscosity was calculated as follows:

$$\text{Inherent viscosity} = \frac{\ln(t/t_o)}{C}$$

wherein t (sec) is the time of fall of the polyurethane solution, $t_o$ (sec) is the time of fall of the solvent and c (g/dl) is the concentration of the polyurethane.

Hydrolytic resistance of polyurethane

Specimens prepared from a 2-mm thick polyurethane sample sheet were immersed in hot water of 100° C. for 10 days, and the strength at break of the films before and after the immersion were compared with each other to obtain a retention ratio, by which hydrolytic resistance was evaluated.

Heat resistance of polyurethane

Specimens prepared from a 2-mm thick polyurethane sheet were tested for dynamic viscoelasticity at a frequency of 11 Hz with a DVE Rheospectra (produced by Rheology Co., Ltd.). The terminal temperature on the high-temperature side of the rubber-like plateau of the dynamic storage elastic modulus was taken as an index of heat resistance.

Cold resistance of polyurethane

Specimens prepared from a 2-mm thick polyurethane sheet were tested for dynamic viscoelasticity at a frequency of 11 Hz with a DVE Rheospectra (produced by Rheology Co., Ltd.) to determine a temperature (Tα) at which the dynamic elasticity loss (E") reached the maximum. The cold resistance was evaluated by Tα.

Mechanical performances of polyurethane

The procedure defined in JIS K 7311 was applied. For example, a 2-mm thick polyurethane sample sheet was obtained by injection molding and dumbbell-shaped test specimens were prepared therefrom. The specimens were tested for tensile strength and elongation at break at an extension rate of 30 cm/min, to evaluate dynamic performance.

Injection moldability of polyurethane

Injection molding was conducted with varying molding cycle times (injection time+cooling time), and the obtained molded articles were tested for determining the molding cycle time at which no sinkmarks or deformations were caused, to evaluate injection moldability.

Tensile strength and elongation of polyurethane fiber

JIS L 1013 was applied.

Elastic recovery of the polyurethane fiber

The polyurethane fiber was elongated to 300% and maintained at that condition for 10 minutes. After the tension was released, the fiber was allowed to stand for 2 minutes and then the length of the resulting fiber was measured to calculate elastic recovery as follows:

$$\text{Elastic recovery} = \{1-(L-L_0)/L_0\} \times 100$$

wherein L is the length of the polyurethane having been allowed to stand for 2 minutes after removal of tension and $L_0$ is the length of the polyurethane before drawing.

Hydrolytic resistance of polyurethane fiber

A polyurethane fiber sample of 40 dr (denier) was allowed to stand under the condition of a natural length at 70° C., 95% RH for 35 days. The fiber was tested for tensile strength at break before and after this exposure. Hydrolytic resistance was evaluated by the retention ratio of the strengths before and after the exposure.

Heat resistance of polyurethane fiber

A polyurethane fiber sample was placed in a heat treatment bath in such a condition that the fiber was elongated to 100% and was gradually heated at a heating rate of 5° C./min from 110° C., to determine a temperature at which the fiber breaks. The heat resistance was evaluated in terms of this temperature.

Resistance to hot water of polyurethane fiber

A polyurethane fiber sample elongated to 300% and kept at the same elongation was subjected to dry heat treatment at 140° C. for 2 minutes, and then treated with hot water at 130° C. under pressure for 30 minutes. Then the stress R (g/80 dr) was measured at 200% elongation. The fiber sample was further tested for measurement of the length directly after releasing the stress and the permanent set represented by S (%) was calculated in accordance with the equation below. The permanent set S is an index showing strain of the sample after hot-water treatment. The smaller the S-value, the more superior the resistance to hot water. On the other hand, the larger the R-value, the more superior the resistance to hot water.

$$S = \{(L-L_0)/2L_0\} \times 100$$

wherein L represents the length of the sample after hot water treatment and $L_0$ represents that before hot water treatment.

Cold resistance of polyurethane fiber 33 to 37 mg of a polyurethane fiber sample of 60 mm long was evenly arranged so as to be 1-mm thick and 5-mm wide and bonded at both ends with an adhesive to prepare the sample specimen. The specimens were tested for dynamic viscoelasticity at a frequency of 11 Hz with a DVE Rheospectra (produced by Rheology Co., Ltd.) to determine a temperature (Tα) at which the dynamic elasticity loss (E") reaches the maximum. The cold resistance was evaluated in terms of Tα.

Color fastness

Color fastness to washing: JIS L 0844A2 was applied,
Color fastness to water: JIS L 0846B was applied.
Color fastness to perspiration: JIS L 0848A was applied.
Color fastness to light: JIS L 0842, the third method for exposure to light, was applied.
Color fastness to chlorine: JIS L 0856 was applied.

The higher the grades of these tests, the more superior the color fastness of the fiber.

Tensile strength and elongation after dyeing

The dyed polyurethane fiber sample was tested for modulus when elongated to 150%, and then the stress during releasing process from 150% elongation was measured. The retention ratio (%) of each value observed against the corresponding value of the polyurethane before dyeing was obtained.

Elastic recovery after dyeing

The dyed polyurethane fiber sample was elongated to 150% and maintained for 10 minutes. After the tension was released, the fiber was allowed to stand for 10 minutes and then the length of the resultant polyurethane fiber was measured to calculate elastic recovery (%) according to the following formula:

$$\text{Elastic recovery} = \{1-(A-A_0)/A_0\} \times 100$$

wherein A represents the length of the polyurethane fiber sample after 10 minutes standing after the tension is released and $A_0$ represents the length of the sample before elongation.

Resistance to chlorine after dyeing

The dyed polyurethane fiber elongated to 50% was immersed as it was elongated, in an aqueous chlorine solution having 335 ppm of effective chlorine concentration and pH=7 at 30° C., for 7 days. Stresses of the polyurethane fibers before and after the immersion in the chlorine solution were determined to calculate the retention ratio of stress after the immersion against that before the immersion. The resistance to chlorine was evaluated by using the above ratio as an index.

The abbreviations of the compounds used in the following Examples and Comparative examples are shown below.

| (Abbreviation) | (Name of compound) |
|---|---|
| 3,8-DMSA | 3,8-dimethyldecanedioic acid |
| 3,7-DMSA | 3,7-dimethyldecanedioic acid |
| AD | adipic acid |
| SB | sebacic acid |
| AZ | azelaic acid |
| DDA | dodecanedioic acid |
| MPA | 3-methylpentanedioic acid |
| MOA | 2-methyloctanedioic acid |
| BD | 1,4-butanediol |
| PD | 1,3-propanediol |
| HD | 1,6-hexanediol |
| MPD | 3-methyl-1,5-pentanediol |
| ND | 1,9-nonanediol |
| MOD | 2-methyl-1,8-octanediol |
| NPG | neopentyl glycol |
| DD | 1,10-decanediol |
| HPD | 1,7-heptanediol |
| MDI | 4,4'-diphenylmethane diisocyanate |

EXAMPLE 1

A 5-L pressure reaction vessel was charged with a solution comprising 83.3 mg of $Rh(CO)_2(CH_3COCHCOCH_3)$, 20.87 g of tris (2,6-di-t-butylphenyl) phosphite and 500 mL of benzene, and the vessel was pressurized to 80 atm with a mixed gas of carbon monoxide/hydrogen (1/1). After the temperature had been elevated to 100° C., 2.05 kg of 2,7-dimethyl-1,7-octadiene was fed thereto over a period of 5 hours, during which the pressure was maintained at 80 atm. After completion of the feed, the reaction was continued for a further 5 hours at the same temperature and pressure. The reaction vessel was cooled and then the gas therein was purged. The reaction mixture was taken out and distilled to remove benzene under a reduced pressure. The resultant residue was purified by distillation to give 3,8-dimethyldecanedial as a colorless clear liquid having a boiling point of 77 to 78 t at 0.2 mmHg. The yield was 56% (1.64 kg).

Analytical data used for structural determination are shown below.

NMR ($CDCl_3$ solvent): $\delta 0.96$ (d, 6H); 1.29 (brs, 8H); 2.05 (m, 2H); 2.18–2.45 (m, 4H); 9.85 (t, 2H) IR: $\nu 2,970$–2,850; 2,730; 1,725; 1,460; 1,380; 1,015 $cm^{-1}$ GC-MS: m/z (relative intensity) 71 (100), 41 (74), 55 (74), 81 (62), 69 (60), 43 (40) 95 (37)

EXAMPLE 2

A 5-L pressure reaction vessel was charged with 0.19 g of $Cu(OCOCH_3)_2(H_2O)$ and 1.5 L of acetic acid, and the vessel was pressurized to 7 atm with air and then warmed to 50° C. While air was introduced at a rate of 240 L/hr, a mixture of 750 g of 3,8-dimethyldecanedial and 750 mL of acetic acid was fed thereto over a period of 3 hours. After completion of the feed, the reaction was conducted for an additional 4 hours at the same temperature and pressure. The reaction vessel was cooled, the gas therein was purged and then the reaction mixture was taken out. This mixture was heated at 110° C. for 1 hour under nitrogen atmosphere. The acetic acid was distilled off under a reduced pressure and the residue was recrystallized twice repeatedly from a mixed solvent of acetic acid/water (1/1), to yield 449 g of 3,8-dimethyldecanedioic acid as a white solid having a melting point of 76.5 to 77.5° C. Additionally, the mother liquid was distilled to remove acetic acid and water, and then recrystallized in the same manner as above to obtain 99 g of 3,8-dimethldecanedioic acid. The total yield of these acid portions was 63%.

Data of instrumental analysis are shown below.

NMR ($CDCl_3$ solvent): $\delta$ 0.97 (d, 6H), 1.28 (brs, 8H); 1.96 (m, 2H); 2.09–2.38 (m, 4H); 10.4 (br) IR (Nujol): $\nu 1,700$ $cm^{-1}$ FAB-MS: m/z (relative intensity) 231 (100), 213 (100).

EXAMPLE 3

A 5-L pressure reaction vessel was charged with a solution comprising 83.3 mg of $Rh(CO)_2(CH_3COCHCOCHS_3)$, 20.87 g of tris(2,6-di-t-butylphenyl) phosphite and 500 mL of benzene, and the vessel was pressurized to 90 atm with a mixed gas of carbon monoxide/hydrogen (1/1). After the temperature had been elevated to 100° C., 2.05 kg of 2,6-dimethyl-1,7-octadiene was added over a period of 5 hours, during which the pressure was maintained at 90 atm. After completion of the feed, the reaction was continued for a further 5 hours at the same temperature and pressure. The reaction vessel was cooled and then the gas therein was purged. The reaction mixture was taken out and then benzene was distilled off under vacuum. The residue was subjected to simple distillation to remove the catalytic components. The resulting distillate was rectified to give 3,7-dimethyldecanedial as an almost colorless liquid having a boiling point of 99° to 100° C. at 0.85 mmHg. The yield was 41% (1.20 kg).

Analytical data used for structural determination are shown below.

NMR ($CDCl_3$ solvent): $\delta 0.89$ (d, 3H); 0.95 (d, 3H); 1.10–1.50 (m, 8H); 1.65 (m, 1H); 2.04 (m, 1H); 2.19–2.47 (m, 4H); 9.85 (m, 2H) IR: $\nu 2,960$–2,850; 2,720; 1,720; 1,455; 1,375 $cm^{-1}$ GC-MS: m/z (relative intensity) 41 (100), 55 (100), 71 (75), 81 (73), 95 (63), 154 (3), 165 (2).

EXAMPLE 4

A 5-L pressure reaction vessel was charged with 0.19 g of $Cu(OCOCH_3)_2(H_2O)$ and 1.5 L of acetic acid, and the vessel was pressurized to 7 atm with air and then warmed to 50° C. While air was introduced at a rate of 240 L/hr, a mixture of 750 g of 3,7-dimethyldecanedial and 750 mL of acetic acid was fed thereto over a period of 3 hours. After completion of the feed, the reaction was conducted for an additional 6 hours at the same temperature and pressure. The reaction vessel was cooled, the gas therein was purged and then the reaction mixture was taken out. This mixture was heated at 110° C. for 1 hour under nitrogen atmosphere. The acetic acid was distilled off under a reduced pressure and the residual liquid was distilled to give 3,7-dimethyldecanedioic acid as an almost colorless clear liquid having a boiling point of 175° to 180° C. at 0.80 mmHg. The yield was 61% (435 g). Instrumental-analysis data are shown below.

NMR ($CDCl_3$ solvent): $\delta 0.89$ (d, 3H); 0.97 (d, 3H); 1.08–1.50 (m, 8H); 1.68 (m, 1H); 1.95 (m, 1H); 2.10–2.42 (m, 4H); 11.4 (br, 2H) IR: $\nu 3,000$–2,850; 2,730; 1,720–1,700; 1,280; 1,220; 930 $cm^{-1}$

EXAMPLES 5 THROUGH 7

A 100-mL pressure reaction vessel was charged with 1.3 mg of $Rh(CO)_2(CH_3COCHCOCH_3)$ 324 mg of tris(2,6-di-t-butylphenyl) phosphite, 20 mL of each of solvents described in Table 1 and 20.0 g of each of dimethyloctadienes represented by the general formula (III) with A and B shown in Table 1, and the vessel was pressurized to 80 atm with a mixed gas of carbon monoxide/hydrogen (1/1). Each of the reaction mixtures was heated to a temperature shown in Table 1, respectively and then heated at the same temperature for 6 hours with stirring while the pressure thereof was maintained at 80 atm. The reaction vessel was cooled and then the gas therein was purged. The reaction mixture taken out was subjected to gas chromatographic analysis. The results show that each dimethyldecanedial represented by the general formula (I) with A and B shown in Table 1 was formed in a yield described in Table 1.

TABLE 1

| Example | Dimethyl-octadiene A | B | Solvent | Temperature (°C.) | Dimethyl-decanedial yield (%) |
|---|---|---|---|---|---|
| 5 | H | CH₃ | isopropyl alcohol | 120 | 51 |
| 6 | H | CH₃ | toluene | 100 | 70 |
| 7 | CH₃ | H | benzene | 120 | 45 |

EXAMPLES 8 THROUGH 11

A 100-mL pressure reaction vessel was charged with 3.5 mg of each one of the metal salts described in Table 2 and 20 mL of acetic acid, and the vessel was pressurized with air to 7 atm, and then heated to a temperature of 50° C. A mixture of 10 g of each of dimethyldecanedials represented by the general formula (I) with A and B shown in Table 2 and 20 g of acetic acid was fed thereto over a period of 20 minutes, while air was introduced at a rate of 5 L/hr. After completion of the feed, the reaction was allowed to continue for an additional 6 hours at the same temperature and pressures. After the reaction vessel had been cooled, the gas therein was purged and then the reaction mixture was taken out. An aliquot of the reaction mixture was esterified and then the resulting mixture was analyzed by gas chromatography, affording a result showing the formation of the dimethyldecanedicarboxylic acids represented by the general formula (II) in a yield as shown in Table 2.

TABLE 2

| Example | Dimethyl-decanedial A | B | Metal salt | Dimethyldecane-dicarboxylic acid yield (%) |
|---|---|---|---|---|
| 8 | H | CH₃ | copper acetate | 85 |
| 9 | H | CH₃ | cobalt acetate | 80 |
| 10 | H | CH₃ | iron acetate | 63 |
| 11 | CH₃ | H | manganese acetate | 55 |

EXAMPLE 12

6900 g of 3,8-dimethyldecanedioic acid and 3240 g of 1,4-butanediol were fed to a reaction vessel and then esterified at 200° C. and atmospheric pressure, while the water that formed was removed out of the system. When the acid value of the reaction mixture became not higher than 30, 134 mg of tetraisopropyl titanate was added thereto and the reaction was allowed to continue while a reduced pressure of 200 to 100 mmHg was maintained. When the acid value reached 1.0, the pressure of the system was further reduced gradually with a vacuum pump and the reaction was completed. After that, the reaction mixture was cooled to 100° C. 180 g of water was added thereto and the mixture was heated with stirring at this temperature for 2 hours to deactivate the titanium-based polycondensation catalyst. Then the water therein was distilled off under reduced pressure. In this way, a polyester diol having a number average molecular weight of 1980, hydroxyl group number of 56.7 and acid value of 0.01 was obtained (hereafter referred as to polyester diol A). As shown in Table 3, the test results for hydrolytic resistance of polyester diol A are very superior.

EXAMPLES 13 THROUGH 22

Polyester diols B through K were obtained by esterification followed by deactivation of the titanium-based polycondensation catalyst, in the same manner as in Example 12 except that the corresponding dicarboxylic acid component and diol component described in Table 3 were used. As shown in table 3, the test results for the polyester diols obtained from Examples 13 through 22 are very good.

TABLE 3

| Example | Polyester diol | Dicarboxylic acid component (mole %) | Diol component (mole %) | Number average molecular weight | Hydrolytic Resistance [acid value (KOH mg/g)] Before hot water treatment | After hot water treatment |
|---|---|---|---|---|---|---|
| Example | | | | | | |
| 12 | A | 3,8-DMSA (100) | BD (100) | 1980 | 0.01 | 0.48 |
| 13 | B | 3,7-DMSA (100) | BD (100) | 1980 | 0.01 | 1.02 |
| 14 | C | 3,8-DMSA/3,7-DMSA (70/30) | BD (100) | 2010 | 0.02 | 0.68 |
| 15 | D | 3,8-DMSA/3,7-DMSA (50/50) | BD (100) | 2030 | 0.03 | 0.82 |
| 16 | E | 3,8-DMSA (100) | PD (100) | 2020 | 0.04 | 0.80 |
| 17 | F | 3,8-DMSA (100) | HD (100) | 2020 | 0.05 | 0.42 |
| 18 | G | 3,8-DMSA (100) | BD/HD (50/50) | 1970 | 0.03 | 0.46 |
| 19 | H | 3,8-DMSA (100) | BD/MPD (50/50) | 2010 | 0.01 | 0.41 |
| 20 | I | 3,8-DMSA/AD (70/30) | BD (100) | 2000 | 0.03 | 1.12 |
| 21 | J | 3,8-DMSA/SB (60/40) | BD (100) | 1990 | 0.03 | 0.98 |
| 22 | K | 3,8-DMSA/AZ (60/40) | BD (100) | 2040 | 0.01 | 1.02 |
| Comparative example | | | | | | |
| 1 | L | 3,8-DMSA/AD (20/80) | BD (100) | 2020 | 0.01 | 30.10 |
| 2 | M | AD (100) | BD (100) | 2010 | 0.02 | >50.00 |

TABLE 3-continued

| Example | Polyester diol | Dicarboxylic acid component (mole %) | Diol component (mole %) | Number average molecular weight | Hydrolytic Resistance [acid value (KOH mg/g)] | |
|---|---|---|---|---|---|---|
| | | | | | Before hot water treatment | After hot water treatment |
| 3 | N | AD (100) | BD/HD (50/50) | 1980 | 0.01 | 15.32 |
| 4 | O | AD (100) | NPG/HD (50/50) | 1990 | 0.01 | 12.06 |
| 5 | P | AD (100) | ND/MOD (65/35) | 2020 | 0.02 | 2.20 |
| 6 | Q | DDA (100) | BD (100) | 1970 | 0.02 | 2.05 |
| 7 | R | MPA (100) | DD (100) | 2010 | 0.02 | 1.90 |
| 8 | S | MOA (100) | HPD (100) | 2020 | 0.01 | 2.00 |

Comparative Examples 1 through 8

Polyester diols L through S were obtained by esterification followed by deactivation of the titanium-based catalyst in the same way as in Example 12 except that the corresponding dicarboxylic acid component and diol component described in Table 3 were used.

Each of the test results with respect to the hydrolytic resistance of the polyester diols L through S was inferior in comparison with those for the polyester diols A through K obtained in Examples 12 through 22. When the polyester diols A through D (Examples 12 through 15) and those Q through S (Comparative examples 6 through 8) are compared, it is understood that the reason why the polyester diol of the present invention is superior in hydrolytic resistance is not the low concentration of the ester group alone, because ratios of acid-value increment of the polyester diols A through D are not more than half of those of the polyester diols Q through S.

EXAMPLES 23 THROUGH 33

Continuous melt polymerization was conducted by feeding continuously, through metering pumps to a same-direction twin-screw extruder (30 mmϕ, L/D=36, set temperature: 200°–250° C.), each of the polyester diols A through K obtained in Examples 12 through 22, 1,4-butanediol and 4,4'-diphenylmethane diisocyanate heat melted at 50° C., in such amounts as to make the molar ratio (polyester diol:1,4-butanediol:4,4'-diphenylmethane diisocyanate) 1:2:3 and at a total rate of 300 g/min. The obtained melts of thermoplastic polyurethane were extruded into water to form a strand, which was then cut with a pelletizer into pellets. The pellets thus obtained were dried at 80° C. for 20 hours. With these dry pellets, injection moldability at 200° C. was evaluated. Further, with 2-mm thick polyurethane sheets prepared by the injection molding at 200° C., the inherent viscosity, hydrolytic resistance, heat resistance, cold resistance and mechanical performance (strength at break and elongation at break) were tested. The results are shown in Table 4.

Comparative Examples 9 through 16

Continuous melt polymerization was conducted by feeding continuously, through metering pumps to a same-direction twin-screw extruder (30 mmϕ, L/D=36, set temperature: 200°–250° C.), each of the polyester diols L through S obtained in Comparative examples 1 through 8, 1,4-butanediol, and 4,4'-diphenylmethane diisocyanate heat melted at 50° C., in such amounts as to make the molar ratio (polyester diol:1,4-butanediol:4,4'-diphenylmethane diisocyanate) 1:2:3 and at a total rate of 300 g/min. The obtained melts of thermoplastic polyurethane were extruded into water to form a strand, which was then cut with a pelletizer into pellets. The pellets thus obtained were dried at 80° C. for 20 hours.

With these dry pellets, injection moldability at 200° C. was evaluated. Further, with 2-mm thick polyurethane sheets prepared by the injection molding at 200° C., the inherent viscosity, hydrolytic resistance, heat resistance, cold resistance and mechanical performance (strength at break and elongation at break) were tested. The results are shown in Table 4.

TABLE 4

| | Raw material of polyurethane | | | Physical properties of polyurethane | | | | | | |
|---|---|---|---|---|---|---|---|---|---|---|
| Example | Polyester diol (molar ratio) | Organic diisocyanate (molar ratio) | Chain extender (molar ratio) | Inherent viscosity (dl/g) | Strength at break (kgf/cm²) | Elongation at break (%) | Hydrolytic Resistance (%) | Heat resistance (°C.) | Cold resistance Tα (°C.) | Injection moldability (sec) |
| Example | | | | | | | | | | |
| 23 | A (1) | MDI (3) | BD (2) | 1.25 | 580 | 600 | 91 | 152 | −46 | 38 |
| 24 | B (1) | MDI (3) | BD (2) | 1.21 | 570 | 610 | 84 | 149 | −46 | 38 |
| 25 | C (1) | MDI (3) | BD (2) | 1.17 | 590 | 590 | 88 | 151 | −46 | 38 |
| 26 | D (1) | MDI (3) | BD (2) | 1.19 | 550 | 620 | 86 | 150 | −46 | 38 |
| 27 | E (1) | MDI (3) | BD (2) | 1.11 | 590 | 630 | 85 | 141 | −44 | 46 |
| 28 | F (1) | MDI (3) | BD (2) | 1.18 | 590 | 570 | 92 | 143 | −46 | 46 |
| 29 | G (1) | MDI (3) | BD (2) | 1.22 | 620 | 580 | 89 | 144 | −46 | 45 |
| 30 | H (1) | MDI (3) | BD (2) | 1.12 | 560 | 620 | 90 | 141 | −47 | 46 |
| 31 | I (1) | MDI (3) | BD (2) | 1.21 | 540 | 580 | 82 | 149 | −43 | 40 |

TABLE 4-continued

| | Raw material of polyurethane | | | Physical properties of polyurethane | | | | | | |
|---|---|---|---|---|---|---|---|---|---|---|
| Example | Polyester diol (molar ratio) | Organic diisocyanate (molar ratio) | Chain extender (molar ratio) | Inherent viscosity (dl/g) | Strength at break (kgf/cm$^2$) | Elongation at break (%) | Hydrolytic Resistance (%) | Heat resistance (°C.) | Cold resistance Tα (°C.) | Injection moldability (sec) |
| 32 | J (1) | MDI (3) | BD (2) | 1.19 | 560 | 590 | 83 | 151 | −42 | 38 |
| 33 | K (1) | MDI (3) | BD (2) | 1.16 | 550 | 570 | 82 | 152 | −42 | 38 |
| Comparative example | | | | | | | | | | |
| 9 | L (1) | MDI (3) | BD (2) | 1.22 | 600 | 560 | 18 | 133 | −35 | 68 |
| 10 | M (1) | MDI (3) | BD (2) | 1.16 | 540 | 550 | 13 | 132 | −34 | 70 |
| 11 | N (1) | MDI (3) | BD (2) | 1.12 | 580 | 530 | 29 | 136 | −34 | 63 |
| 12 | O (1) | MDI (3) | BD (2) | 1.19 | 530 | 560 | 32 | 129 | −25 | 72 |
| 13 | P (1) | MDI (3) | BD (2) | 1.29 | 590 | 580 | 56 | 139 | −40 | 60 |
| 14 | Q (1) | MDI (3) | BD (2) | 1.11 | 580 | 500 | 58 | 141 | 10 | 52 |
| 15 | R (1) | MDI (3) | BD (2) | 1.20 | 580 | 530 | 63 | 137 | −22 | 55 |
| 16 | S (1) | MDI (3) | BD (2) | 1.23 | 570 | 520 | 55 | 136 | −28 | 56 |

As clearly shown from the results given in Table 4, compared with the polyurethanes of Comparative examples 9 through 16, the polyurethanes of Examples 23 through 33 using the polyester diols A through K, which contain 30 mole % or more of 3,8-dimethyldecanedioic acid unit and/or 3,7-dimethyldecanedioic acid units in the dicarboxylic acid units, are not only very excellent in hydrolytic resistance, but are also excellent in heat resistance, cold resistance and injection moldability without spoiling dynamic performance such as strength at break and elongation at break. It is understood that the polyurethanes using, particularly, a polyester diol containing 1,4-butanediol as a diol component are more superior in heat resistance and injection moldability. In the case of the polyurethane of Comparative Example 9, which uses a polyester diol containing only 20 mole of 3,8-dimethyldecanedioic acid units in the dicarboxylic acid units, the mechanical performance, such as strength at break and elongation at break, is almost in the same level as those of the polyurethanes of Example 23 through 33. However, the hydrolytic resistance, heat resistance, cold resistance and injection moldability are inferior when compared with those of Examples 23 through 33. Compared with the polyurethanes of Examples 23 through 33, the polyurethanes (Comparative examples 15 and 16) obtained by using the polyester diols which contain a branched dicarboxylic acid component (3-methylpentanedioic acid unit or 2-methyloctanedioic acid unit) in the same concentration of ester groups as those of the polyester diols A through D are inferior in hydrolytic resistance, heat resistance, cold resistance and injection moldability.

EXAMPLES 34 THROUGH 38

Continuous melt polymerization was conducted by feeding continuously, through metering pumps to a same direction twin-screw extruder (30 mmφ, L/D=36, set temperature: 200°–250° C.), each of the polyester diols A, C, D, J and K obtained in Examples 12, 14, 15, 21 and 22, 1,4-butanediol, and 4,4'-diphenylmethane diisocyanate heat melted at 50° C., in such amounts as to make the molar ratio (polyester diol:1,4butanediol:4,4'-diphenylmethane diisocyanate) 1:2:3.09 and at a total rate of 300 g/min. The formed polyurethane was fed directly to a spinning machine and spun at a spinning temperature of 220° C., a dew point of cooling wind of 10° C. and a spinning speed of 500 m/min, to give a polyurethane yarn of 40 denier/1 filament. The yarn thus obtained was aged at 90° C. for 12 hours under a humidity of dew point of −30° C., further continuously aged at 25° C. for 3 days under a humidity of 50%, and then tested for physical properties. The results are shown in Table 6. Furthermore, the polyurethane fiber obtained above was knitted into a knit fabric with a circular knitting machine (gauge 20). The knit fabric was dyed under conditions as described in Table 5. The dyed knit fabric was washed thoroughly with water, dried and then tested for color fastness and physical properties. The results are shown in Table 7.

TABLE 5

| dyeing conditions |
|---|
| Scouring under relaxation |
| at 80° C. for 1 minute. |
| Dyeing |
| Dyeing machine: Drum type dyeing machine |
| Composition of dyeing agent: |
| Dye: Sumikaron Red-E-RPD quinone-type, made by Sumitomo Chemical Co., Ltd.) — 2.0% owf |
| Dispersion assistant: Disper TL (manufactured by Meisei Chemical Co., Ltd.) — 1 g/liter |
| pH regulator: ammonium sulfate — 1 g/liter |
| acetic acid — 1 g/liter |
| Bath ratio: 1:30 |
| Dyeing temperature: Temperature elevated from 40° C. to 130° C. over 30 minutes and kept at this temperature for another 30 minutes |
| Reduction cleaning |
| Reduction liquor composition: |
| soda hydrosulfite — 3 g/liter |
| soda ash — 2 g/liter |
| Amiladin (made by Dai-Ichi Kogyo Seiyaku Co., Ltd.) — 1 g/liter |
| Bath ratio: 1:30 |
| Cleaning Temperature: 80° C. for 20 minutes |

TABLE 6

| Example | Raw material of polyurethane | | | Physical properties of polyurethane | | | | | | | | |
|---|---|---|---|---|---|---|---|---|---|---|---|---|
| | Polyester diol (molar ratio) | Organic diisocyanate (molar ratio) | Chain extender (molar ratio) | Inherent viscosity (dl/g) | Tensile strength (g/dr) | Elongation (%) | Elastic recovery (%) | Hydrolytic Resistance (%) | Heat resistance (°C.) | Resistance to hot water R (g/80 dr) | S (%) | Cold resistance Tα (°C.) |
| Example | | | | | | | | | | | | |
| 34 | A (1) | MDI (3.09) | BD (2) | 1.23 | 1.7 | 490 | 94 | 92 | 185 | 1.9 | 60 | −46 |
| 35 | C (1) | MDI (3.09) | BD (2) | 1.20 | 1.5 | 500 | 94 | 90 | 183 | 1.9 | 60 | −46 |
| 36 | D (1) | MDI (3.09) | BD (2) | 1.18 | 1.4 | 480 | 93 | 89 | 182 | 1.8 | 61 | −46 |
| 37 | J (1) | MDI (3.09) | BD (2) | 1.19 | 1.6 | 490 | 92 | 85 | 182 | 1.6 | 63 | −42 |
| 38 | K (1) | MDI (3.09) | BD (2) | 1.15 | 1.3 | 470 | 92 | 84 | 180 | 1.6 | 63 | −42 |
| Comparative example | | | | | | | | | | | | |
| 17 | L (1) | MDI (3.09) | BD (2) | 1.22 | 1.5 | 460 | 89 | 54 | 175 | 1.0 | 71 | −35 |
| 18 | M (1) | MDI (3.09) | BD (2) | 1.16 | 1.4 | 490 | 92 | 32 | 161 | 0.6 | 83 | −34 |
| 19 | Q (1) | MDI (3.09) | BD (2) | 1.10 | 1.3 | 380 | 80 | 70 | 174 | 1.1 | 69 | 10 |
| 20 | R (1) | MDI (3.09) | BD (2) | 1.11 | 1.4 | 410 | 88 | 76 | 172 | 1.1 | 68 | −23 |
| 21 | S (1) | MDI (3.09) | BD (2) | 1.17 | 1.5 | 420 | 84 | 68 | 175 | 1.2 | 67 | −26 |

TABLE 7

| Example | Color fastness of polyurethane fiber to | | | | | Physical properties of polyurethane fiber after dyeing | | | |
|---|---|---|---|---|---|---|---|---|---|
| | Washing (class) | Water (class) | Perspiration (class) | Light (class) | Chlorine (class) | Retention of elongation (%) | Retention of stress (%) | Elastic recovery (%) | Resistance to chlorine (%) |
| Example | | | | | | | | | |
| 34 | 4–5 | 4–5 | 4–5 | 4–5 | 4–5 | 98 | 97 | 98 | 99 |
| 35 | 4–5 | 4–5 | 4–5 | 4–5 | 4–5 | 97 | 96 | 98 | 98 |
| 36 | 4–5 | 4–5 | 4–5 | 4–5 | 4–5 | 97 | 95 | 97 | 98 |
| 37 | 4–5 | 4–5 | 4–5 | 4–5 | 4–5 | 95 | 95 | 96 | 97 |
| 38 | 4–5 | 4–5 | 4–5 | 4–5 | 4–5 | 95 | 95 | 96 | 96 |
| Comparative example | | | | | | | | | |
| 17 | 2–3 | 2–3 | 2–3 | 3 | 3 | 50 | 43 | 80 | 40 |
| 18 | 2 | 2 | 2 | 2 | 2 | —* | —* | —* | —* |
| 19 | 3–4 | 3–4 | 3–4 | 3–4 | 3–4 | 80 | 75 | 88 | 75 |
| 20 | 3–4 | 3–4 | 3–4 | 3–4 | 3–4 | 85 | 81 | 91 | 82 |
| 21 | 3–4 | 3–4 | 3–4 | 3–4 | 3–4 | 79 | 73 | 89 | 76 |

*: Not measurable due to breaking polyurethane fiber during measurement.

Comparative Example 17 through 21

Polyurethane fibers were produced in the same manner as in Examples 34 through 38 except for using each of the polyester diols L, M, Q, R and S obtained in Comparative examples 1, 2, 6, 7 and 8 as the polyester diol, and the fibers thus obtained were tested for physical properties. The results are shown in Table 6. Furthermore, after dyeing, washing with water and drying in the same manner as in Examples 34 through 38, the physical properties of the polyester fiber after dyeing were tested. The results are shown in Table 7.

As clearly seen in Tables 6 and Table 7, compared with the polyurethane fibers of Comparative examples 17 through 21, the polyurethane fibers of Examples 34 through 38 (using the polyester diols A, C, D, J and K, which contain 30 mole % or more of 3,8-dimethyldecanedioic acid units and/or 3,7-dimethyldecanedioic acid units in the dicarboxylic acid units) are excellent not only in hydrolytic resistance but also in resistance to hot water, heat resistance and cold resistance without spoiling their mechanical performance such as strength and elongation. Further, the color fastnesses of the polyurethane fibers of the present invention are all Class 4 to 5, clearing Class 3 which is generally required for clothing, and are therefore excellent. In addition, the physical properties of the polyurethane fiber after dyeing are also superior.

In the case of the polyurethane fiber of Comparative Example 17 which uses the polyester diol L containing only 20 mole % of 3,8-dimethyldecanedioic acid units in the dicarboxylic acid units, the strength and elongation is almost at the same level as those of the polyurethane fibers of Examples 34 through 38, but the hydrolytic resistance and resistance to hot water are inferior when compared with those of Examples 34 through 38. Furthermore, the color fastness and physical properties of the polyurethane fibers after dyeing are also inferior.

Compared with the polyester fibers of Examples 34 through 38, the polyurethane fiber of Comparative example 18 which uses the polyester diol M having a high ester-group-concentration is not only extremely inferior in hydrolytic resistance, but also inferior in resistance to hot water, heat resistance and cold resistance. Furthermore, the physical properties of the polyurethane after dyeing are very inferior.

Compared with the polyurethane fibers of Examples 33 through 38, the polyurethane fiber of Comparative example 19, which uses the polyester diol Q having the same ester group concentration as those of the polyesters A, C, D, J and K, is somewhat inferior in hydrolytic resistance, and also inferior in elastic recovery, cold resistance and elongation. Furthermore, the physical properties of the polyester after dyeing are also inferior.

Compared with the polyurethane fibers of Example 34 through 38, the polyurethane fiber of Comparative examples 20 or 21 which uses the polyester diol R or S containing the dicarboxylic acid unit having single methyl-branch (3-methylpentanedioic acid unit or 2-methyloctanedioic acid unit) is inferior in heat resistance, cold resistance, elongation and hydrolytic resistance. Furthermore, the physical properties of the polyurethane after dyeing are also inferior.

This application is based on Japanese Patent Applications 282006/1994, 327291/1994 and 44079/1995, filed with the Japanese Patent Office on Nov. 16, 1994, Dec. 28, 1994 and Mar. 3, 1995, respectively, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A polyurethane comprising polyester diol units, organic diisocyanate units and units from a chain extender, wherein said polyester diol units comprise dicarboxylic acid units and diol units, wherein at least 30 mole % of said dicarboxylic acid units are units derived from 3,8-dimethyldecanedioic acid, 3,7-dimethyldecanedioic acid or a mixture thereof, and wherein said polyester diol units have a number-average molecular weight in a range from 500 to 6000.

2. The polyurethane according to claim 1, wherein said diol units comprise 30 mole % or more of diol units derived from 1,4-butanediol.

3. The polyurethane according to claim 1, wherein the polyurethane has an inherent viscosity of from 0.3 to 2.0 dl/g.

4. A molded article comprising the polyurethane according to claim 1.

5. A fiber, comprising the polyurethane according to claim 1.

* * * * *